(12) United States Patent
Asaad et al.

(10) Patent No.: US 11,684,781 B2
(45) Date of Patent: Jun. 27, 2023

(54) BRAIN IMPLANTABLE DEVICE

(71) Applicants: BROWN UNIVERSITY, Providence, RI (US); RHODE ISLAND HOSPITAL, Providence, RI (US)

(72) Inventors: Wael Farouk Asaad, Westwood, MA (US); Shane Lee, Providence, RI (US); Peter Maxwell Lauro, Providence, RI (US)

(73) Assignees: Brown University, Providence, RI (US); Rhode Island Hospital, Providence, RI (US)

( * ) Notice: Subject to any disclaimer, the term of this patent is extended or adjusted under 35 U.S.C. 154(b) by 0 days.

(21) Appl. No.: 17/470,710

(22) Filed: Sep. 9, 2021

(65) Prior Publication Data

US 2022/0072314 A1 Mar. 10, 2022

Related U.S. Application Data

(60) Provisional application No. 63/076,453, filed on Sep. 10, 2020.

(51) Int. Cl.
  *A61N 1/36* (2006.01)
  *A61N 1/05* (2006.01)
  *A61N 1/372* (2006.01)
  *A61N 1/378* (2006.01)

(52) U.S. Cl.
  CPC ....... *A61N 1/36139* (2013.01); *A61N 1/0534* (2013.01); *A61N 1/378* (2013.01); *A61N 1/37211* (2013.01)

(58) Field of Classification Search
  CPC .............. A61N 1/0534; A61N 1/36125; A61N 1/36139; A61N 1/37211; A61N 1/378
  See application file for complete search history.

(56) References Cited

U.S. PATENT DOCUMENTS

| | | |
|---|---|---|
| 7,983,757 B2 | 7/2011 | Miyazawa et al. |
| 8,788,044 B2 | 7/2014 | John |
| 8,892,208 B2 | 11/2014 | Flynn et al. |
| 8,914,115 B2 | 12/2014 | Giftakis et al. |
| 8,914,119 B2 | 12/2014 | Wu et al. |
| 9,782,590 B2 | 10/2017 | O'Connell et al. |
| 10,195,438 B2 | 2/2019 | Libbus et al. |
| 10,463,860 B2 | 11/2019 | Sinclair et al. |
| 10,632,311 B2 | 4/2020 | Giftakis et al. |
| 2013/0150918 A1 | 6/2013 | Peterson et al. |

(Continued)

FOREIGN PATENT DOCUMENTS

WO 2020/043635 A2 3/2020

OTHER PUBLICATIONS

Haddock, Andrew J., "Data-Driven Optimization of Deep Brain Stimulation for Movement Disorders", University of Washington, 2017, 135 pages.

*Primary Examiner* — Brian T Gedeon
(74) *Attorney, Agent, or Firm* — Adler Pollock & Sheehan P.C.

(57) ABSTRACT

A system includes intracranial electrodes embedded into a cranium, a deep brain stimulation system embedded into the cranium, a brain implantable device embedded into the cranium, and a pulse generator, the deep brain stimulation system and the brain implantable device linked to the intracranial electrodes and to the pulse generator.

11 Claims, 2 Drawing Sheets

(56) References Cited

U.S. PATENT DOCUMENTS

| | | | |
|---|---|---|---|
| 2016/0166326 A1* | 6/2016 | Bakker | A61N 1/372 606/129 |
| 2016/0287126 A1 | 10/2016 | Parker et al. | |
| 2018/0229046 A1 | 8/2018 | Parker et al. | |
| 2020/0108253 A1 | 4/2020 | Crowder et al. | |

* cited by examiner

BRAIN IMPLANTABLE DEVICE

CROSS REFERENCE TO RELATED APPLICATIONS

This application claims benefit from U.S. Provisional Patent Application Ser. No. 63/076,453, filed Sep. 10, 2020, which is incorporated by reference in its entirety.

STATEMENT REGARDING GOVERNMENT INTEREST

None.

BACKGROUND OF THE INVENTION

The present invention relates generally to treatment of neurologic disease, and more particularly to a brain implantable device.

In general, the treatment of neurologic disease is severely limited by the quality and granularity of data regarding patients' "in the wild" disease burden and response to treatment. The patient experience is filtered through a patient's own subjective recollection and understanding of their condition, and clinicians must interpret these accounts to infer disease burden and response to therapy, and then make adjustments to therapy as deemed necessary based upon these imperfect data. Neural activity biomarkers of disease, monitored chronically, can potentially augment clinical judgment by providing objective data regarding disease burden and response to therapy in a patient's natural environment. Furthermore, these biomarkers may be used to derive control signals for neuromodulation (e.g., closed-loop deep brain stimulation) that regulate disease manifestations in real-time.

However, current implantable neuromodulation devices are limited in their recording and stimulation capabilities, and have minimal on-board processing to implement sophisticated models for transforming neural activity biomarkers to appropriate stimulation patterns.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In an aspect, the invention features a system including intracranial electrodes embedded into a cranium, a deep brain stimulation system embedded into the cranium, a brain implantable device embedded into the cranium, and a pulse generator, the deep brain stimulation system and the brain implantable device linked to the intracranial electrodes and to the pulse generator.

In another aspect, the invention features a system including intracranial electrodes embedded into a cranium, a brain implantable device embedded into the cranium, and a pulse generator, the brain implantable device linked to the intracranial electrodes and to the pulse generator.

In still another aspect, the invention features a brain implantable device including an input unit, a switch, a power conditioning and buffering unit, a stimulation waveform generator and amplifier array unit, a main logic board, an input/output unit, a signal acquisition and program filtering unit, and a memory.

The details of one or more embodiments of the invention are set forth in the accompanying drawings and the description below. Other features and advantages of the invention will become apparent from the description and the drawings, and from the claims.

DETAILED DESCRIPTION

Figure 1:
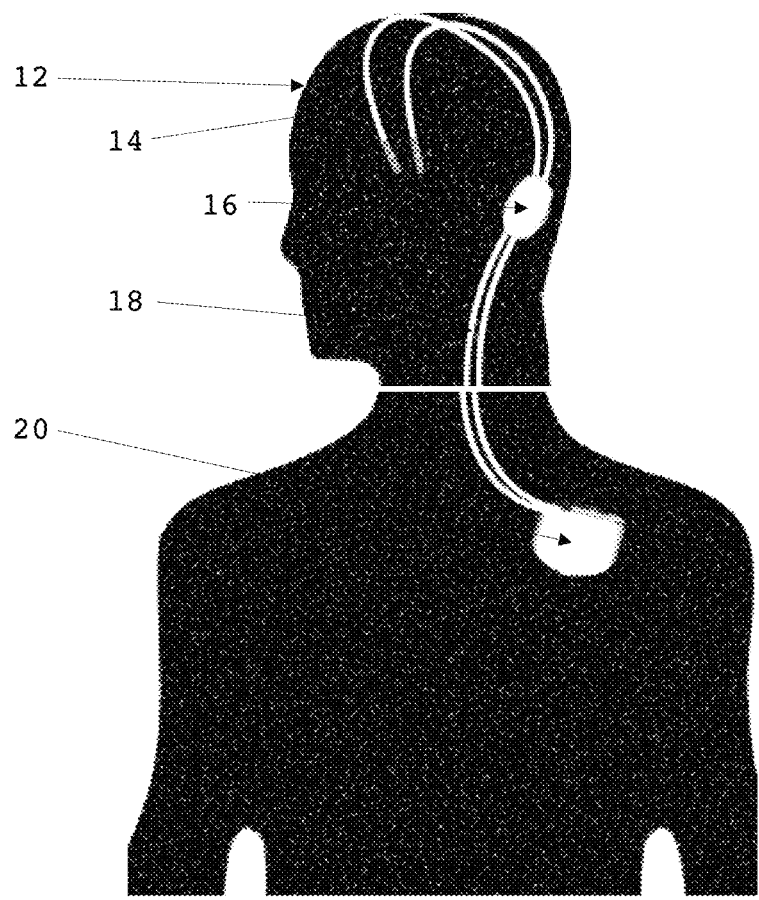
FIG. 1 is an illustration of an embedded exemplary discovery device.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Given the growing acceptance and utilization of deep brain stimulation for a variety of disorders, ranging from movement disorders such as Parkinson's Disease to epilepsy to obsessive compulsive disorder (and many more potential indications in clinical trials), this presents an opportunity to interface with the human brain in potentially thousands of individuals, to expand the basic knowledge and improve the treatment of neurologic disease, if harnessed appropriately.

The brain implantable device described herein, also referred to as a "discovery device," augments traditional deep brain stimulation systems to expand the capability of those systems to better detect and understand neural activity biomarkers, and to implement more complex, patient-specific algorithms for neuromodulation therapy. In this way, the relatively large experience of deep brain stimulation can be leveraged.

As shown in FIG. 1, in a preferred embodiment, an embedded exemplary brain implantable device 16, also referred to herein as a "discovery device," is implanted in a brain 12 alongside intracranial electrodes 14. The discovery device 16 is linked to a pulse generator battery 20 with extensions 18. In FIG. 1, the discovery device 16 is implanted alongside a standard deep brain stimulation system with relatively little modification of a surgical procedure, and is capable of superseding or overriding the function of the standard deep brain stimulation system under controlled circumstances to enable enhanced acquisition of neural signals and testing of novel algorithms for brain stimulation.

In one alternate embodiment, implantation of the discovery device 16 is done without the standard deep brain stimulator system, as a stand-alone device for recording neural activity and/or delivering stimulation, when coupled with an appropriate neural tissue interface (e.g., depth electrode for neural signal acquisition or electrical stimulation, electrochemical probe for measuring levels of molecules of interest, such as neurotransmitters or pathologic byproducts of disease, and so forth). The capabilities of the discovery device 16 would include those necessary for electrochemical measurement, such as cyclic voltammetry. Thus, the discovery device 16 can serve as a robust, general purpose neuromodulation test-bed.

Figure 2:
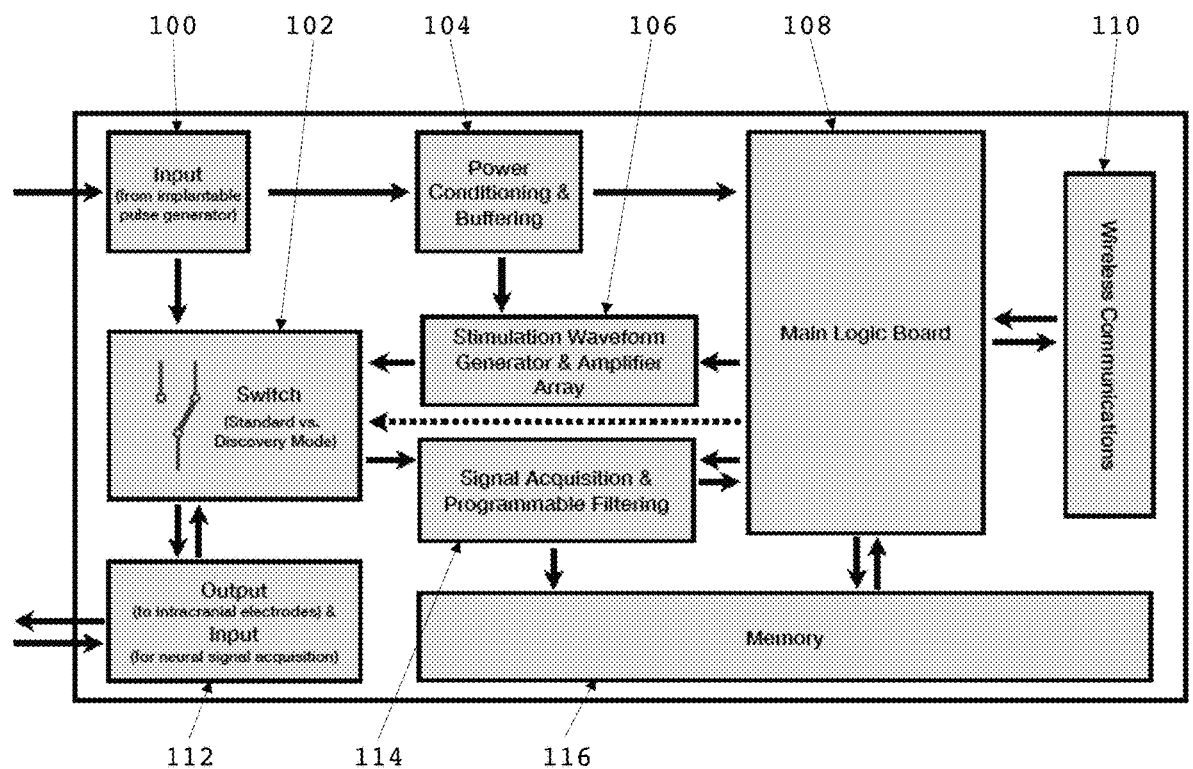
FIG. 2 is a block diagram of the discovery device.

As shown in FIG. 2, in one implementation, the discovery device 16 includes an input unit 100, a switch 102, a power conditioning and buffering unit 104, a stimulation waveform generator and amplifier array unit 106 and a main logic board 108. The discovery device 16 also includes an input/output unit 112, a signal acquisition and program filtering unit 114 and a unit 116 and a memory 116.

The switch 102 enables at least two primary modes of operation, i.e., a "standard mode" and a "discovery mode." In standard mode, the discovery device 16 acts as a simple pass-through, enabling traditional neuromodulation protocols to be implemented, as programmed into the standard, existing pulse generator battery system. Input from the pulse generator battery 20 is received by the input unit 100, sent through the switch 102 to the input/output unit 112 and on to the intracranial electrodes 14.

In research (also referred to as "discovery mode") mode, the discovery device 16 receives power from the pulse generator battery 20, but records neural activity and delivery stimulation based upon its own on-board algorithms, programmed using separate, device-specific telemetry.

One purpose of the discovery device 16 is serve as a "discovery engine" for a wide variety of neurologic conditions, ranging from those already approved for clinical use, those currently under investigation, and new neurologic indications that would benefit from objective disease tracking and/or neuromodulation.

As shown and described above, the discovery device 16 is implanted alongside a traditional, existing, FDA approved device. As such, the discovery device 16 is powered by the traditional, existing, FDA-approved clinical deep brain stimulation (DBS) pulse generator battery. The discovery device 16 includes a switch to toggle between a "pass-through" mode and a "discovery" mode.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A system comprising:
   intracranial electrodes configured to be embedded into a cranium;
   a deep brain stimulation system configured to be embedded into the cranium;
   a brain implantable device configured to be embedded into the cranium; and
   a pulse generator outside of the cranium, the deep brain stimulation system and the brain implantable device linked to the intracranial electrodes and to the pulse generator.

2. The system of claim 1 wherein the brain implantable device is configured to supersede or override a function of the deep brain stimulation system under controlled circumstances to enable enhanced acquisition of neural signals and testing of novel algorithms for brain stimulation.

3. The system of claim 2 wherein the brain implantable device comprises:
   an input unit;
   a switch;
   a power conditioning and buffering unit;
   a stimulation waveform generator and amplifier array unit;
   a main logic board;
   an input/output unit;
   a signal acquisition and program filtering unit; and
   a memory.

4. A system comprising:
   intracranial electrodes configured to be embedded into a cranium;
   a brain implantable device configured to be embedded into the cranium; and
   a pulse generator outside of the cranium, the brain implantable device linked to the intracranial electrodes and to the pulse generator, and wherein the brain implantable device is configured to supersede or override to enable enhanced acquisition of neural signals and testing of novel algorithms for brain stimulation.

5. The system of claim 4 wherein the brain implantable device comprises:
   an input unit;
   a switch;
   a power conditioning and buffering unit;
   a stimulation waveform generator and amplifier array unit;
   a main logic board;
   an input/output unit;
   a signal acquisition and program filtering unit; and
   a memory.

6. The system of claim 5 further comprising a standard deep brain stimulation system configured to be embedded into the cranium alongside the brain implantable device.

7. The system of claim 6 wherein the switch enables toggling between a pass-through mode and a discovery mode.

8. The system of claim 7 wherein the pass-through mode enables traditional neuromodulation protocols to be implemented.

9. The system of claim 8 wherein the discovery mode enables recording of neural activity and delivery stimulation based upon the brain implantable device's own on-board algorithms, programmed using separate, device-specific telemetry.

10. A brain implantable device comprising:
    an input unit;
    a switch;
    a power conditioning and buffering unit;
    a stimulation waveform generator and amplifier array unit;
    a main logic board;
    an input/output unit;
    a signal acquisition and program filtering unit; and
    a memory, wherein the brain implantable device is configured to supersede or override to enable enhanced acquisition of neural signals and testing of novel algorithms for brain stimulation.

11. The brain implantable device of claim 10 wherein the input unit is configured to receive power from an implantable pulse generator.

* * * * *